United States Patent
Ajay

(10) Patent No.: US 12,253,503 B2
(45) Date of Patent: Mar. 18, 2025

(54) MODULAR ASPIRATED SMOKE, GAS, OR AIR QUALITY MONITORING SYSTEMS AND DEVICES

(71) Applicant: Honeywell International Inc., Charlotte, NC (US)

(72) Inventor: Kemal Ajay, Mount Waverly (AU)

(73) Assignee: Honeywell International Inc., Charlotte, NC (US)

( * ) Notice: Subject to any disclaimer, the term of this patent is extended or adjusted under 35 U.S.C. 154(b) by 160 days.

(21) Appl. No.: 17/501,432

(22) Filed: Oct. 14, 2021

(65) Prior Publication Data
US 2022/0120723 A1    Apr. 21, 2022

Related U.S. Application Data

(60) Provisional application No. 63/093,209, filed on Oct. 17, 2020.

(51) Int. Cl.
| | | |
|---|---|---|
| *G08B 17/10* | (2006.01) | |
| *G01N 1/26* | (2006.01) | |
| *G01N 33/00* | (2006.01) | |

(52) U.S. Cl.
CPC ........... *G01N 33/0022* (2013.01); *G01N 1/26* (2013.01); *G01N 33/0031* (2013.01)

(58) Field of Classification Search
CPC .. G01N 33/0022; G01N 1/26; G01N 33/0031; G01N 33/0009; G01N 1/24; G08B 17/117; B01D 46/4227; B01D 46/442; B01D 2258/0283; B01D 2258/06
USPC ........................................................ 340/628
See application file for complete search history.

(56) References Cited

U.S. PATENT DOCUMENTS

| | | | | |
|---|---|---|---|---|
| 5,000,052 A | * | 3/1991 | Sipin | G01N 1/2202 |
| | | | | 73/863.03 |
| 5,103,212 A | * | 4/1992 | Notarianni | G01N 1/26 |
| | | | | 340/628 |
| 5,552,775 A | | 9/1996 | Harley | |
| 5,713,856 A | * | 2/1998 | Eggers | G16H 70/40 |
| | | | | 604/65 |
| 8,742,939 B2 | | 6/2014 | Polak et al. | |

(Continued)

FOREIGN PATENT DOCUMENTS

| | | |
|---|---|---|
| AU | 2015323977 B2 | 7/2020 |
| CN | 108732309 A | 11/2018 |

(Continued)

OTHER PUBLICATIONS

Extended European Search Report for related European Application No. 21202993.8, mailed Mar. 18, 2022 (9 pgs).

(Continued)

*Primary Examiner* — Tai T Nguyen
(74) *Attorney, Agent, or Firm* — Brooks, Cameron & Huebsch, PLLC

(57) ABSTRACT

Devices, methods, and systems for a modular aspirated smoke, gas, or air quality monitoring system are described herein. One modular monitoring unit, includes a base having a plurality of sampling tubes mounted thereon, at least one pump, and at least one detector module that is releasably attached to the base, wherein the pump draws air from one of the sampling tubes into a particulate sensing chamber within the detector module.

20 Claims, 9 Drawing Sheets

(56) References Cited

U.S. PATENT DOCUMENTS

| | | | |
|---|---|---|---|
| 9,208,671 B2 | 12/2015 | Susel et al. | |
| 10,495,618 B2 | 12/2019 | Williamson | |
| 2007/0008157 A1* | 1/2007 | Siemens | G08B 17/10 |
| | | | 340/628 |
| 2007/0113686 A1* | 5/2007 | Desrochers | G01N 1/22 |
| | | | 73/863.33 |
| 2014/0375464 A1 | 12/2014 | Caragata | |
| 2016/0116389 A1* | 4/2016 | Cooper | G01N 15/0227 |
| | | | 356/340 |
| 2017/0292912 A1* | 10/2017 | Ho | G01N 15/00 |
| 2022/0375801 A1* | 11/2022 | Chen | H01L 21/67253 |

FOREIGN PATENT DOCUMENTS

| | | |
|---|---|---|
| CN | 304975954 | 1/2019 |
| CN | 305365939 | 9/2019 |

OTHER PUBLICATIONS

"Multi-channel aspirating smoke detector", https://pim.firesecurityproducts.com/sites/default/files/1138_modulaser_airsense_brochure_en_2019_lr.pdf, 2019, 8 pages.

* cited by examiner

MODULAR ASPIRATED SMOKE, GAS, OR AIR QUALITY MONITORING SYSTEMS AND DEVICES

TECHNICAL FIELD

The present disclosure relates generally to modular devices and systems for aspirated smoke, gas, or air quality monitoring.

BACKGROUND

Some smoke detection systems have a number of sample points spaced around a building that are connected via sampling tubes to a remotely located single central detector apparatus that samples air taken from the sample points to determine if smoke or a fire is present in an area of the building. For example, such systems may be referred to as very early smoke detection apparatus (VESDA) systems.

DETAILED DESCRIPTION

Figure 1:
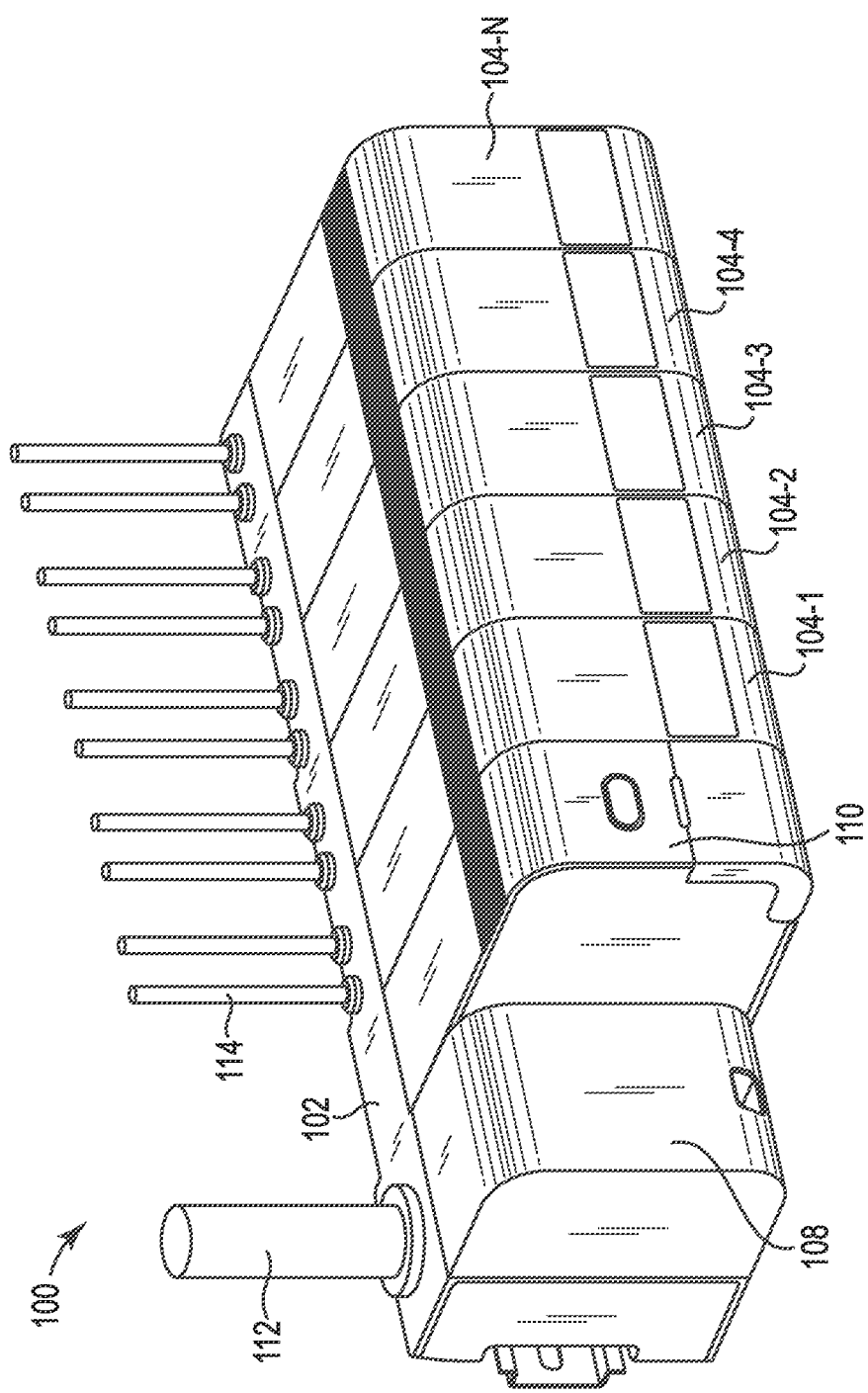
FIG. 1 is an illustration of a perspective view of a modular aspirated smoke, gas, or air quality monitoring system device in accordance with an embodiment of the present disclosure.

The present disclosure relates to modular aspirated smoke, gas, or air quality monitoring systems and devices. Embodiments of the present disclosure use tubes to sample air, smoke, and/or gas from locations in a building.

There are multiple embodiments of the system proposed. In one embodiment, a system has an individual air pump which draws air through the sampling tubes and/or through the sensing components of a detector module. In some embodiments, each detector module (which has two small tubes associated with it, in the embodiment shown in FIG. 3A) can have one pump per sampling tube. In another embodiment, a system has a common pump which provides overall pumping to draw air through a plurality (e.g., all) of the sampling tubes.

In some embodiments, the system has detector modules that can be individually removed and/or replaced. This can be beneficial as individual modules can be selectively removed for maintenance or repair without having to disconnect the sampling tubes. In such embodiments, the sampling tubes can be connected to the base of the device (the device is also referred to as a unit herein) and the modules can have releasable connections to the connectors on the base that can be reconnected when a replacement module is positioned, thereby reconnecting the sampling tubes associated with the module to the replacement module.

In various embodiments, each module has an air filter associated with it. The filter traps contaminants drawn in through the sampled air. This reduces or prevents contaminants, such as dust, pollen, viruses, undesirable chemicals, and bacteria, from being circulated through a building.

In some implementations, the air filter is detachable and/or replaceable from the detector module without having to remove the detector module itself. This can be beneficial as the technician does not have to disassemble the detector module, saving timing and the possibility of an error occurring during reassembly.

For common pump embodiments: The pump can be a module which can be readily removed and replaced if it fails, without having to dismantle any other parts of the system.

The pump also can be a module which can be sized in power and air flow capacity to suit the number of tubes and the length of tubes connected to the pump. That is, different capacity pump modules can be plugged in to suit different installed tube configurations which saves cost and power.

In such an embodiment, there can be a common vacuum manifold running from the pump along the inside of the rear mounting of the module. This structure enables a common vacuum pump to engage simply without having to have individual pump vacuum connections going to each module.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure and should not be taken in a limiting sense.

The figures herein follow a numbering convention in which the first digit or digits correspond to the drawing figure number and the remaining digits identify an element or component in the drawing.

As used herein, "a", "an", or "a number of" something can refer to one or more such things, while "a plurality of"

something can refer to more than one such things. For example, "a number of components" can refer to one or more components, while "a plurality of components" can refer to more than one component.

FIG. 1 is an illustration of a perspective view of a modular aspirated smoke, gas, or air quality monitoring system device in accordance with an embodiment of the present disclosure. As shown in FIG. 1, the modular aspirated smoke, gas, or air quality monitoring system device 100 includes a base 102 onto which a number of detector modules 104 are attached thereto. The base 102 includes a number of components thereon. For example, the base includes a cable conduit 112 (large tube) that allows cabling to be routed through the interior of the conduit and connected to the modular aspirated smoke, gas, or air quality monitoring system device via an aperture in the device.

The cable conduit 112 connects to a cable management module 108 portion of the base 102. The cable management module 108 has a housing with a cover to keep connections for power and data communication to and from the device out of sight and secure from tampering. The cable conduit also provides those functions. In the embodiment of FIG. 1, the cable management module is located on the left side of the device, however, the embodiments of the present disclosure are not so limited.

In the embodiment of FIG. 1, next to the cable management module is a communications module 110. The communications module 110 includes an easy access reset button (316 of FIG. 3) on the front. The communication module 110 also can include other operational buttons and/or dials within the housing and a cover (318 of FIG. 3) to also keep them out of sight and secure from tampering. In some embodiments, the cover can be or have a portion that is at least partially translucent, allowing a technician to see the status of the buttons/dials (e.g., their current settings), so the technician can see their status, but the buttons/dials are not accessible to be tampered with.

In some embodiments, the covers of one or more modules of the modular aspirated smoke, gas, or air quality monitoring system device can be secured such that they need to be removed by a tool (specialized tool carried by a technician). In this manner, it is likely that those wishing to tamper with the modular aspirated smoke, gas, or air quality monitoring system device will not be able to access the internal components of the modules.

On the right side of the modular aspirated smoke, gas, or air quality monitoring system device illustrated in FIG. 1, a number of detector modules 104-1 . . . 104-N (referred to generally as modules 104) are provided. These detector modules each contain one or more sensors that sense one or more environmental elements in the sampled air moving through the one or more tubes connected to the detector. Sensors can, for example, detect particulate, such as smoke particles, or gases, such as carbon monoxide, carbon dioxide, and/or detect other environmental elements that may indicate less than desirable air quality.

In the embodiment illustrated in FIG. 1, each detector 104 is connected to multiple channels/tubes 114. The modular aspirated smoke, gas, or air quality monitoring system device embodiment illustrated in FIG. 1 also includes five detector modules 104 each having two channels, meaning this device can sample on ten channels, however the number of modules and/or channels per module is not so limited. The embodiment of FIG. 1 also includes a mounting bracket 150 for mounting the device to a wall or rack.

Figure 2:
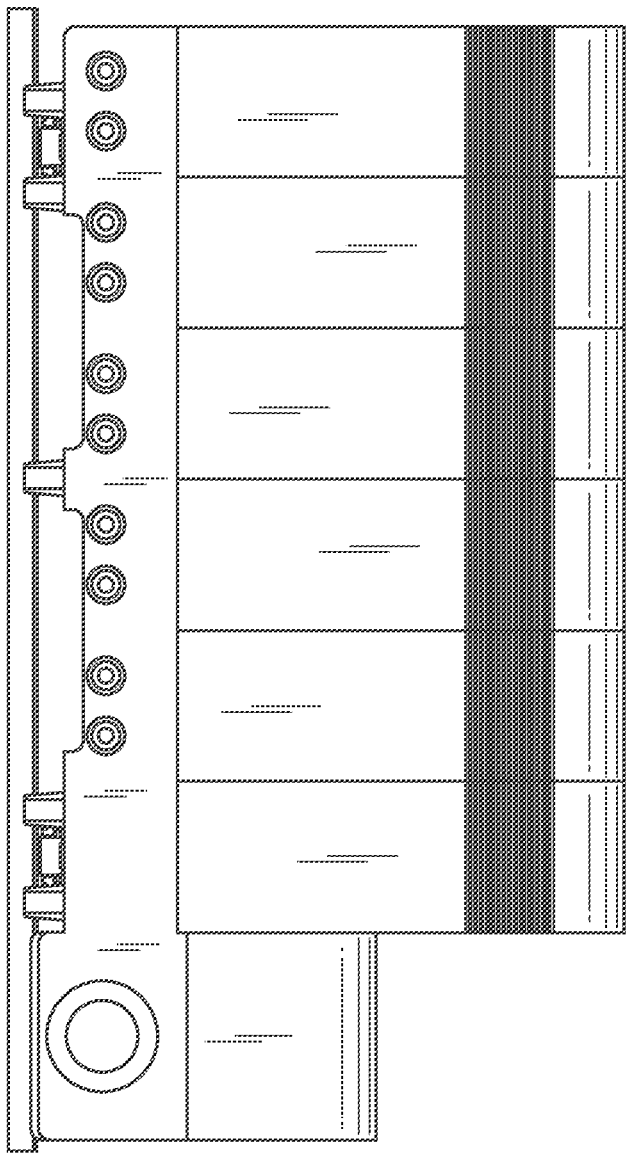
FIG. 2 is an illustration of a top view of a modular aspirated smoke, gas, or air quality monitoring system device in accordance with an embodiment of the present disclosure.
Figure 4:
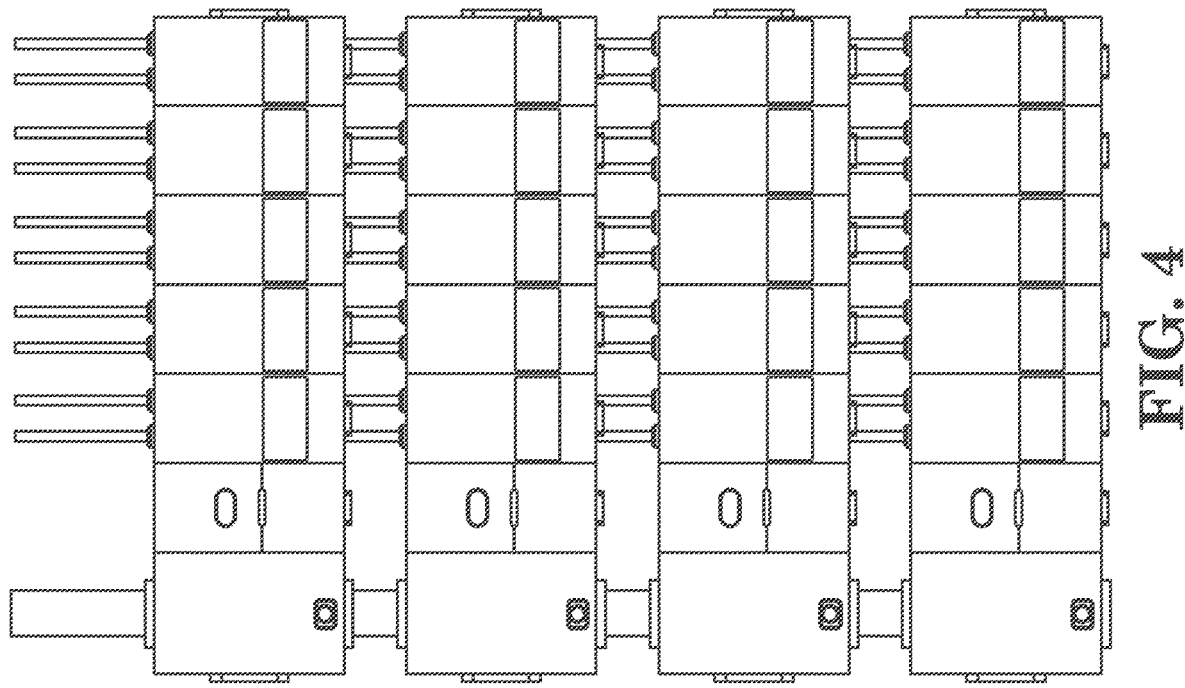
FIG. 4 is an illustration of a front view of a rack of multiple modular aspirated smoke, gas, or air quality monitoring system devices in accordance with an embodiment of the present disclosure.
Figure 8:
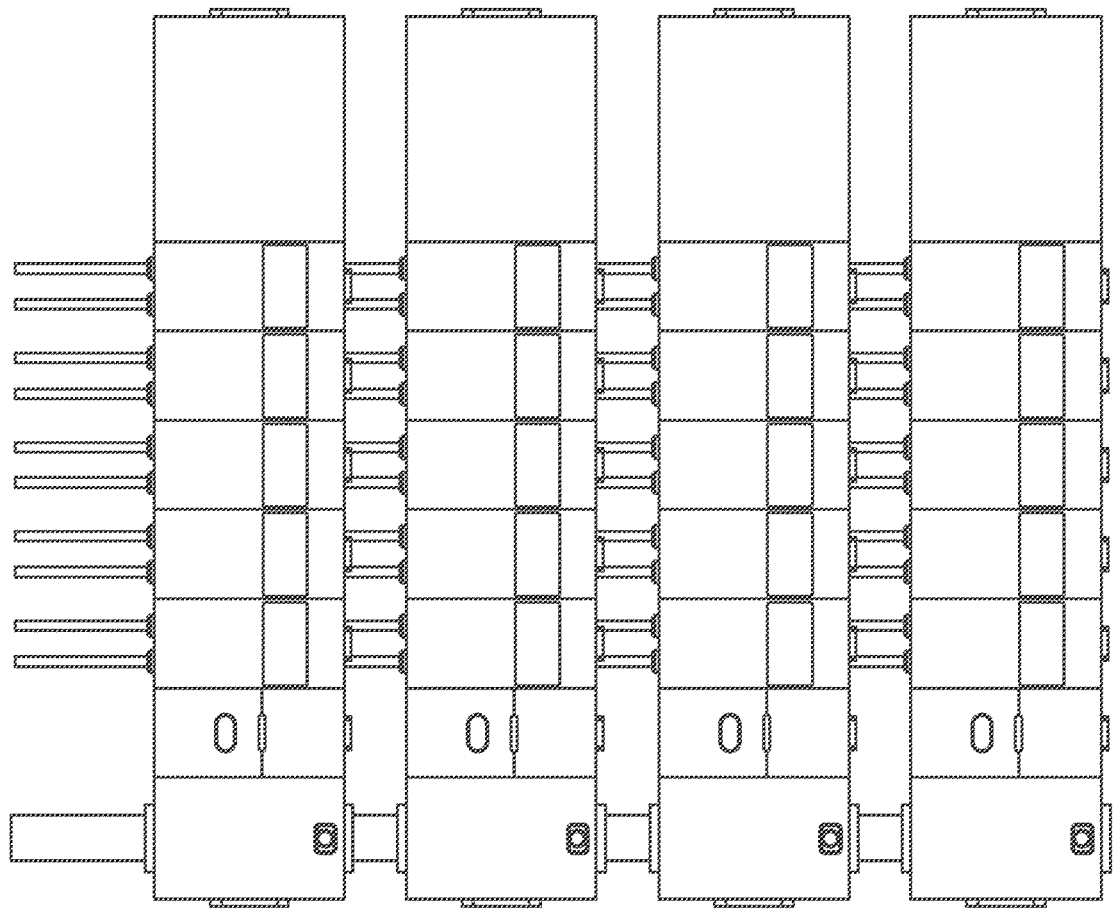
FIG. 8 is an illustration of a front view of a rack of multiple modular aspirated smoke, gas, or air quality monitoring system devices in accordance with an embodiment of the present disclosure.

FIG. 2 is an illustration of a top view of a modular aspirated smoke, gas, or air quality monitoring system device in accordance with an embodiment of the present disclosure. FIG. 2 shows the cable conduit 212 mounted to the top of the base 202 behind the cable management module 208 and the multiple sampling tubes 214 connected to the top of the base 202. In this embodiment, the tubes 214 are arranged such that the tubes are provided in pairs with each pair aligned with a detector module 204. The embodiment of FIG. 2 also includes a mounting bracket 250 that can be used to mount the modular aspirated smoke, gas, or air quality monitoring system device to a wall or to a wall mounted rack, as illustrated in FIGS. 4 and 8.

Figure 3A:
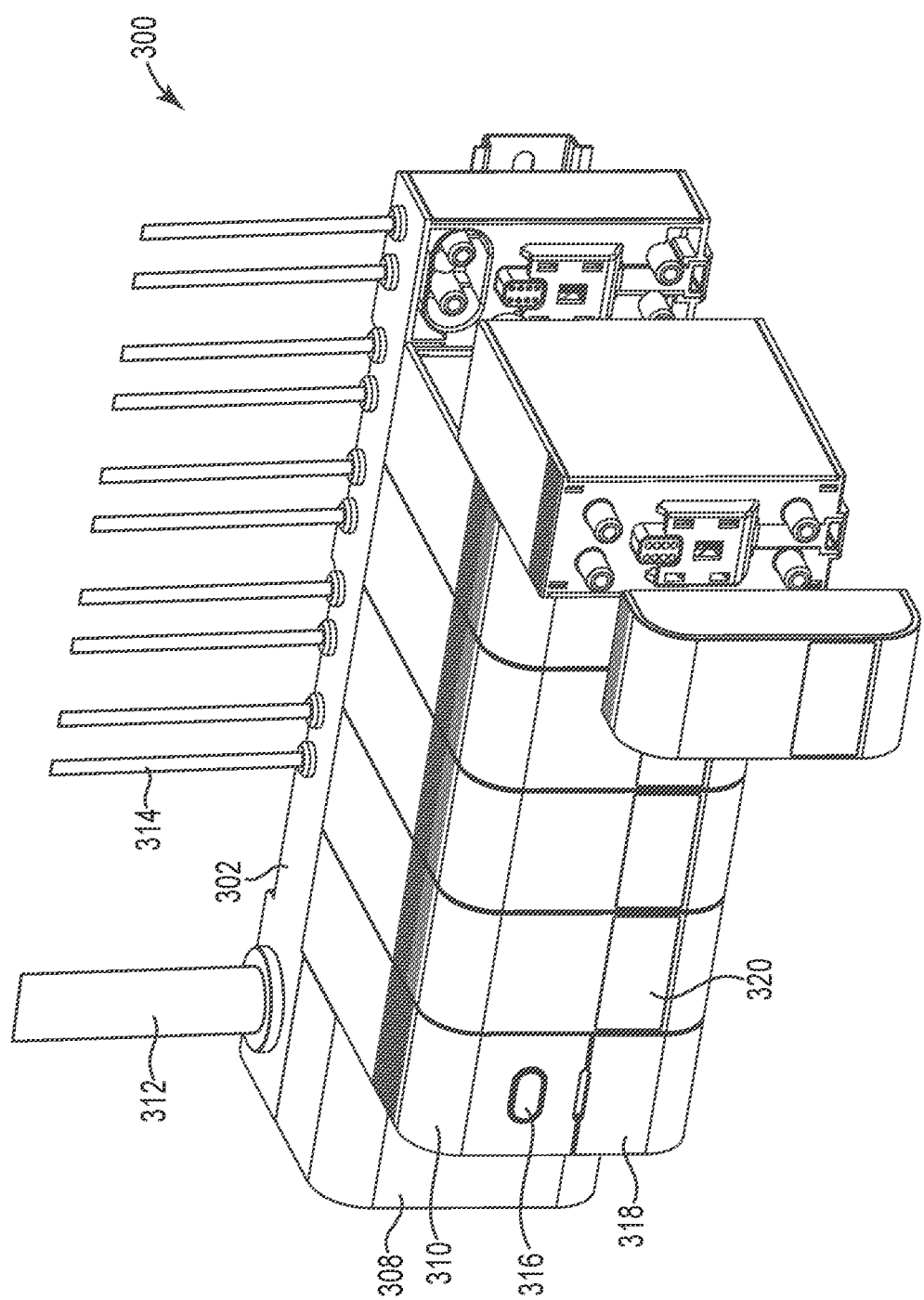
FIG. 3A is an illustration of a perspective view of a modular aspirated smoke, gas, or air quality monitoring system device with one of the detector modules removed in accordance with an embodiment of the present disclosure.

FIG. 3A is an illustration of a perspective view of a modular aspirated smoke, gas, or air quality monitoring system device with one of the detector modules removed in accordance with an embodiment of the present disclosure. As in FIG. 1, FIG. 3A also shows the cable conduit 312, the cable management module 308 and the communication module 310, with reset button 316 and cover 318. FIG. 3A also provides a more detailed view of the interior components of the base as well as the detector module and its filter module/cover.

As shown in FIG. 3A, the detector modules are independently removeable from the base 302 of system 300. Each detector module also has a cover thereon that is removable. The cover can have a display 320 that indicates a status condition of the individual detector. In some embodiments, the cover can be a filter module as described in more detail below.

FIG. 3A also illustrates that the base 302 can have a number of tube connections that connect the tubes 314 to its associated detector module and circuitry connections for providing connections for power and data transmission purposes of the components of the module, such as for sensing components and data collection. Similar connections are also shown on the front surface of the detector. These connections can be used for attachment of other modules that can be added on (e.g., gas sensing module and/or air quality module, added to a smoke sensing module) to the detector module. In the embodiment of FIG. 3A the base 302 can include a pump to facilitate movement of air through the tubes 314 and through the modules 304. FIG. 3A also shows the mounting bracket 350 attached to the back side of the base 302.

In some embodiments, each detector module can also have a filter that can be removed from the detector module without disassembling the detector module. Such functionality can thereby save the technician's time during maintenance of the system.

Figure 3B:
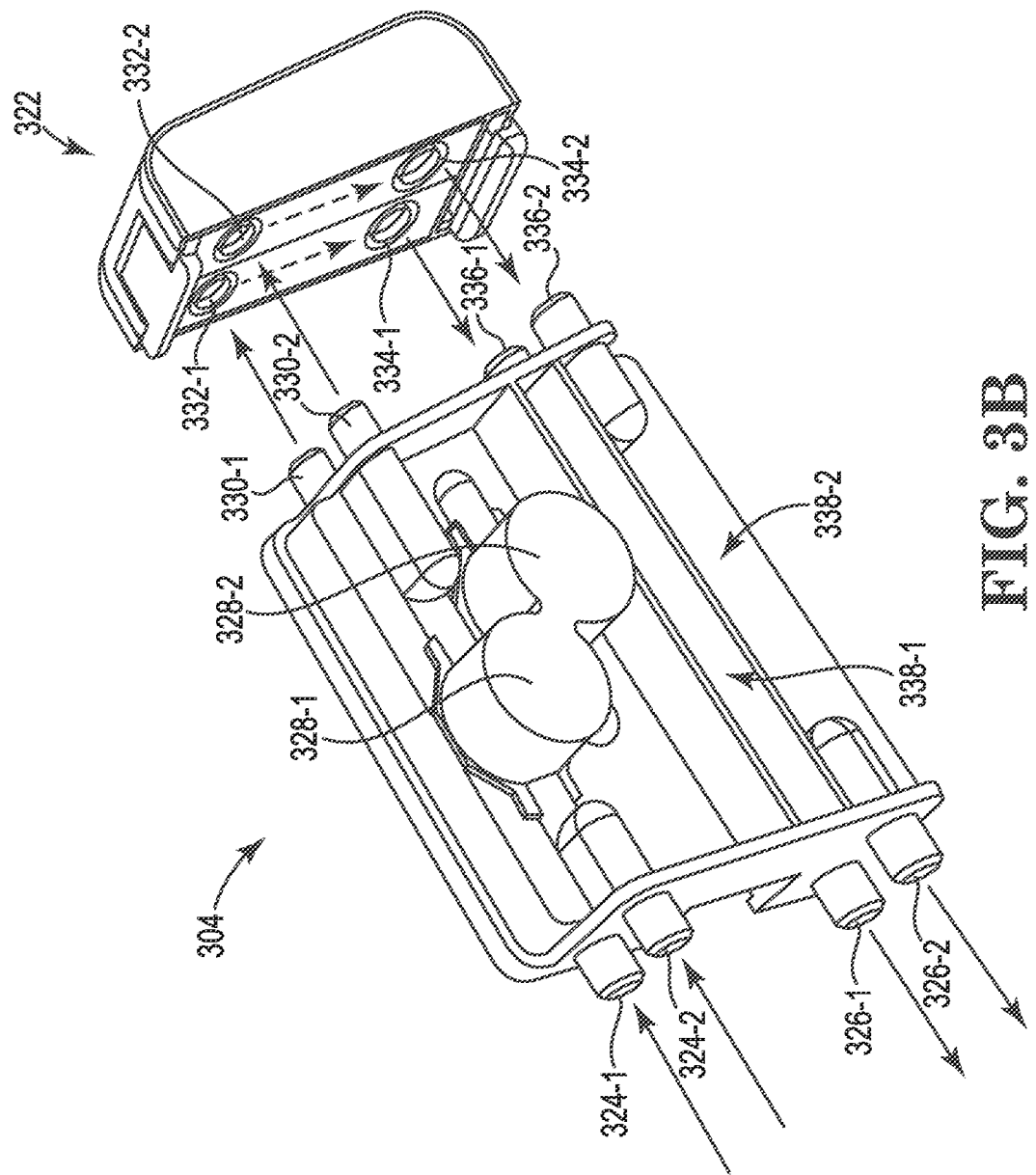
FIG. 3B is an illustration of a perspective view of a detector module of a modular aspirated smoke, gas, or air quality monitoring system device in accordance with an embodiment of the present disclosure.

FIG. 3B is an illustration of a perspective view of a detector module of a modular aspirated smoke, gas, or air quality monitoring system device in accordance with an embodiment of the present disclosure. In the embodiment illustrated in FIG. 3B, the module 304 has multiple particulate sensing chamber inlets 324-1 and 324-2, multiple particulate sensing chambers 328-1 and 328-2, multiple particulate sensing chamber outlets 330-1 and 330-2, multiple flow sensing chamber inlets 336-1 and 336-2, multiple flow sensing chambers 338-1 and 338-2, and multiple flow sensing chamber outlets 326-1 and 326-2. The embodiment of FIG. 3B also shows the removable filter 322 having multiple inlets 332-1 and 332-2 and outlets 334-1 and 334-2.

In use, the module 304 is connected, via inlets 324 and outlets 326 to corresponding inlet and outlet ports of the base 302 of FIG. 3A, such that the air to be tested can be communicated from tubes 314 to the module 304. A first air sampling path is represented by components 324-1, 328-1, 330-1, 332-1, 334-1, 336-1, 338-1, and 326-1; while a second air sampling path is represented by components 324-2, 328-2, 330-2, 332-2, 334-2, 336-2, 338-2, and 326-2.

As can be understood from the layout of the module shown, in the embodiments of FIGS. 3A and 3B, the module 304 including the filtering cap 322 can be used with air from two sampling tubes 314. However, some embodiments may have more or less air sampling paths designed therein.

Each air sampling path draws air in from one of the tubes 314 and tests the air to see if it contains smoke, undesired chemicals, or a threshold level of particulate (by using a sensor in the particulate sensing chamber designed to identify one or more such particles). Additionally, being modular in design, the sensors can be easily changed to repurpose a unit to sense a different type of particle which can be beneficial in some implementations.

Once the air has passed through the particulate chamber, it passes out through the outlet 330 and into the inlet 332 of the filter. The filter reduces or removes the amount of particulate in the air as this particulate may be harmful or may contaminate the device or area around the device if not removed or reduced.

Once filtered, the air exits the outlet 334 of the filter 322 and enters the inlet 336 of the flow sensing chamber 338. The flow sensor determines that a threshold level of air is passing through the air sampling path (e.g., from the space being sampled). This information can be utilized, for example, to determine whether the device is operating correctly and whether the particulate sensing data is accurate, among other uses for the data. Once the air has passed through the flow sensing chamber, it exits the module through outlet 326.

One additional benefit of the modular nature of the design shown in FIG. 3B is that the filter can be easily changed if it becomes dirty or no longer effective for filtering a desired particle. Also, if a different particle is to be filtered, the filter can easily be removed and replaced by a different filter. This can also be the case where a different threshold of filtration is desired. A user can simply remove the current filter 322 and replace it with one that will filter more or less of the desired particulate.

FIG. 4 is an illustration of a front view of a rack of multiple modular aspirated smoke, gas, or air quality monitoring system devices in accordance with an embodiment of the present disclosure. In the embodiment of FIG. 4, multiple modular aspirated smoke, gas, or air quality monitoring system devices are mounted together on a rack that can be mounted to a wall or the devices can be mounted to the wall directly without a rack.

The modular nature of this system design allows the system to be easily expanded to include monitoring of more channels. For example, the embodiment shown in FIG. 4 can accommodated 40 channels (2 channels per detector module×5 modules=10 channels per modular aspirated smoke, gas, or air quality monitoring system device×four devices provided on the rack=40 channels). Embodiments of the present disclosure are not limited to this configuration and more or less channels/detector module, detector modules/device, and/or devices/rack could be utilized.

In the arrangement illustrated in FIG. 4, the first cable conduit section can run into the top of a first cable management module of a first modular aspirated smoke, gas, or air quality monitoring system device, via an aperture in the top of the first cable management module. The first modular aspirated smoke, gas, or air quality monitoring system device can also have an aperture in the bottom of the first cable management module 412-1 and a second section of the cable conduit 412-2 can be positioned between the first modular aspirated smoke, gas, or air quality monitoring system device and a second modular aspirated smoke, gas, or air quality monitoring system device such that the second section of the cable conduit runs into the top of the cable management module of the second modular aspirated smoke, gas, or air quality monitoring system device. In this manner, the communications and power connections (e.g., power cord, data cable) to the modular aspirated smoke, gas, or air quality monitoring system can be secured between the devices (e.g., between devices 400-1, 400-2, 400-3, 400-L via conduit sections 412-1, 412-2, 412-3, 412-L).

It should be noted that although illustrated in a similar manner, the sampling tubes are not connected between devices in FIG. 4, but rather run from each detector to a particular location (e.g., a different location for each tube) within the building that is to be monitored. In such an arrangement, the mounting bracket and/or shape of the back of the modular aspirated smoke, gas, or air quality monitoring system device can be designed to allow space for the passage of the tubes from other devices on the rack to pass behind the modular aspirated smoke, gas, or air quality monitoring system devices.

Such a design feature can be seen in FIG. 2 where the back on the device has a number of recesses formed therein to provide a number of gaps 252 between the back of the device 254 and the front of the mounting bracket 256. These gaps can be sized and shaped to allow tubes from the device and other devices to pass behind the device shown in FIG. 2.

Figure 5:
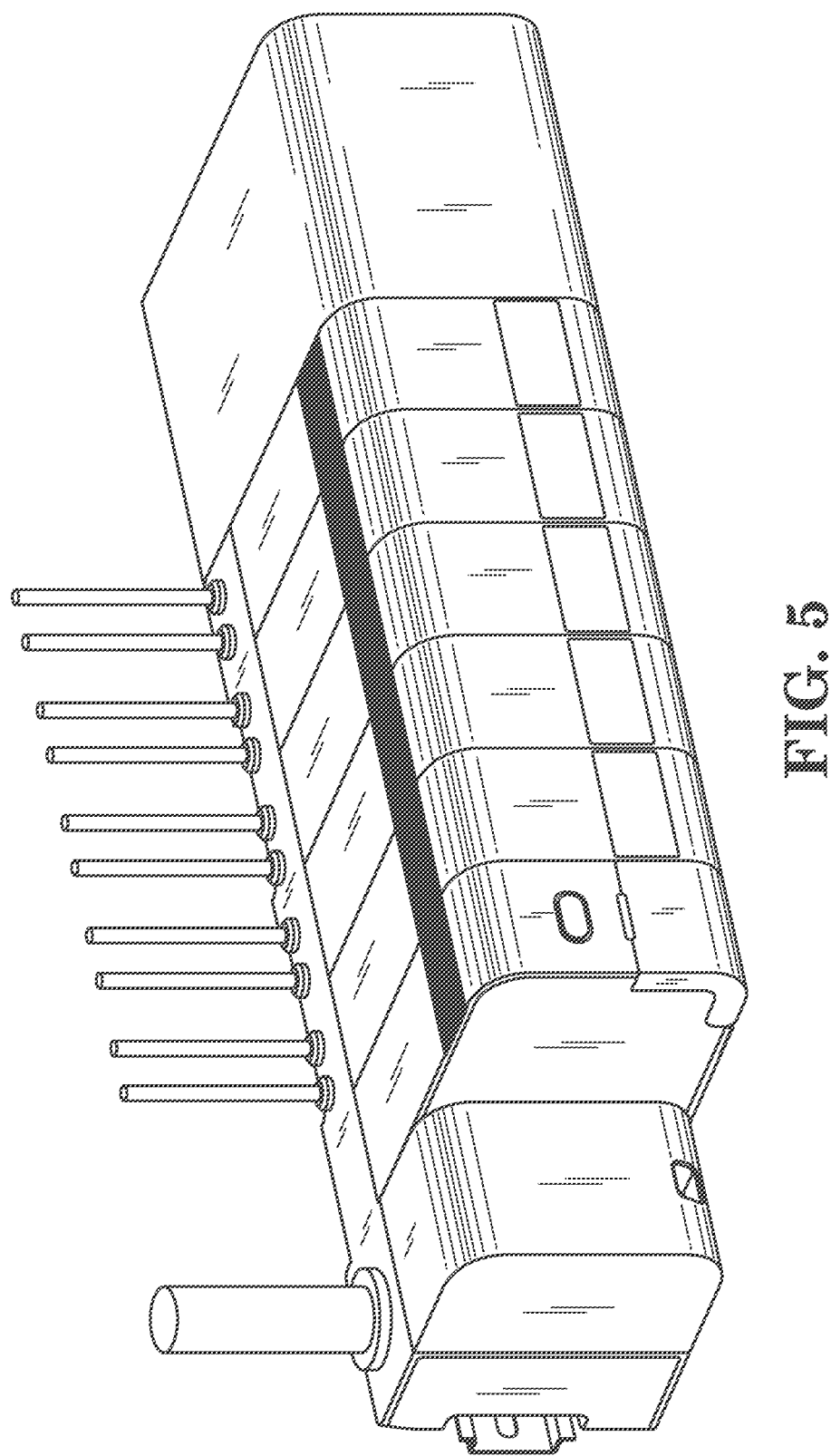
FIG. 5 is an illustration of a perspective view of a modular aspirated smoke, gas, or air quality monitoring system device in accordance with an embodiment of the present disclosure.

FIG. 5 is an illustration of a perspective view of a modular aspirated smoke, gas, or air quality monitoring system device in accordance with an embodiment of the present disclosure. In the embodiment of FIG. 5, the modular aspirated smoke, gas, or air quality monitoring system device includes a pumping module (606 in FIG. 6). In this implementation, this pumping module provides air flow through the tubes and detector modules for all of the system rather than having separate pumps for each detector and its associated tubes.

Figure 6:
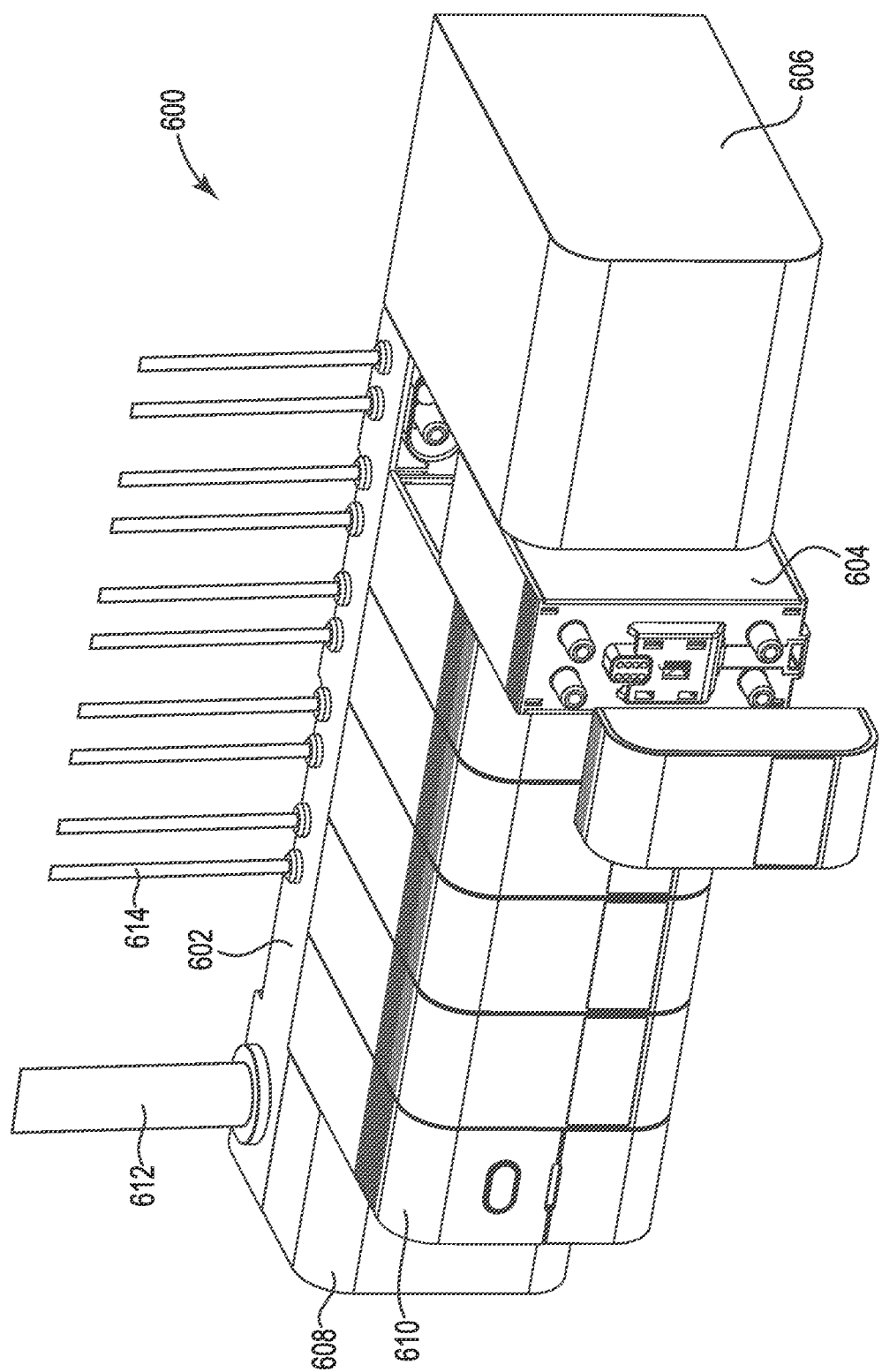
FIG. 6 is an illustration of a perspective view of a modular aspirated smoke, gas, or air quality monitoring system device with one of the detector modules removed in accordance with an embodiment of the present disclosure.

FIG. 6 is an illustration of a perspective view of a modular aspirated smoke, gas, or air quality monitoring system device with one of the detector modules removed in accordance with an embodiment of the present disclosure. The embodiment shown in FIG. 6 is similar to the embodiment shown in FIG. 3A, in that the system 601 has: a base 602 with a cable management module 608 connected to a cable conduit 612, connections to one or more sampling tubes 614, a communication module 610, and a number of detector modules 604. However, the embodiment of FIG. 6 also includes the pumping module 606.

In the arrangement shown, the pumping module 606 is attached at the right of the detector modules 604, but it could be positioned elsewhere on the device (e.g., between communication module 610 and the left-most detector module (e.g., 104-1 of FIG. 1)). Additionally, the pumping module 606 may be connected to the base 602 and/or to the mounting bracket.

Figure 7:
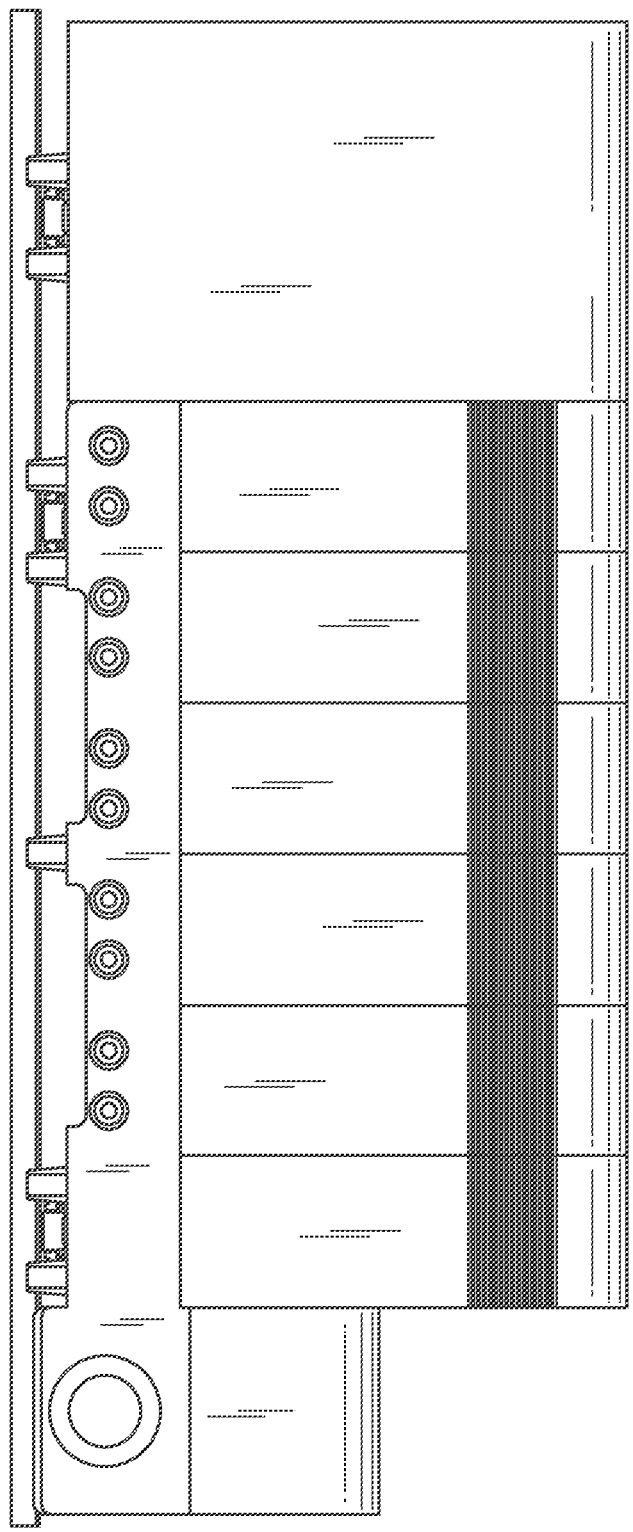
FIG. 7 is an illustration of a top view of a modular aspirated smoke, gas, or air quality monitoring system device in accordance with an embodiment of the present disclosure.

FIG. 7 is an illustration of a top view of a modular aspirated smoke, gas, or air quality monitoring system device in accordance with an embodiment of the present disclosure. Similar to FIG. 2, FIG. 7 shows the cable conduit mounted to the top of the base behind the cable management module and the multiple sampling tubes connected to the top of the base 702, but also shows that this device includes a pumping module 706. The embodiment of FIG. 7 also includes a mounting bracket that can be used to mount the modular aspirated smoke, gas, or air quality monitoring system device 701 to a wall or to a wall mounted rack, as illustrated in FIG. 8.

FIG. 8 is an illustration of a front view of a rack of multiple modular aspirated smoke, gas, or air quality monitoring system devices in accordance with an embodiment of the present disclosure. In the embodiment of FIG. 8, multiple modular aspirated smoke, gas, or air quality monitoring system devices (801-1, 801-2, 801-3, 801-M) each having a pumping module 806 (806-1, 806-2, 806-3, 806-M) are mounted together on a rack that can be mounted to a wall or the devices can be mounted to the wall directly without a rack. As with the above rack structure of FIG. 4, the modular nature of this system design allows the system to be easily expanded to include monitoring of more channels. Again, here the cable conduit can be expanded to include sections between the other devices of the rack and the sampling tubes can be accommodated behind the devices.

The embodiments of the present disclosure provide greater flexibility in creating a modular aspirated smoke, gas, or air quality monitoring system by allowing components to be part of a modular system, but to be independently replaceable or, in some cases, upgradable. Additionally, embodiments allow for a greater ability to expand the system in an organized, modular fashion. The embodiments of the present disclosure also provide a system that reduces technician time and system down time.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A modular monitoring unit, comprising:
a base having a plurality of sampling tubes mounted thereon;
at least one pump; and
a plurality of detector modules, each sampling tube of the base is in fluid communication with a different air sampling path that progresses through a detector module of the plurality of detector modules, each detector module of the plurality of detector modules is connected via one or more inlet ports and one or more outlet ports thereon to corresponding inlet and outlet ports of the base, such that air to be tested is communicated from each sampling tube attached to the base to an air sampling path within the detector module to which it has a fluid connection and that each detector module is each independently releasably attached to the base, wherein the at least one pump draws the air from one of the plurality of sampling tubes into the air sampling path and into a particulate sensing chamber within the detector module.

2. The modular monitoring unit of claim 1, wherein each detector module has a pump for drawing the air from one of the plurality of sampling tubes into the particulate sensing chamber within the detector module.

3. The modular monitoring unit of claim 1, wherein the at least one pump is positioned within a pump module that is releasably attached to the base.

4. The modular monitoring unit of claim 1, wherein the base includes a backing plate for attachment of the base to a vertical surface.

5. The modular monitoring unit of claim 4, wherein the plurality of sampling tubes pass between a front surface of a mounting plate and a back surface of the base.

6. The modular monitoring unit of claim 1, wherein the base includes a conduit for positioning of at least one of: a power cord and a communication cable.

7. The modular monitoring unit of claim 1, wherein the detector module has a plurality of particulate sensing chambers therein.

8. A modular monitoring unit, comprising:
a base having apertures for a connection of a plurality of sampling tubes mounted thereto;
at least one pump; and
a plurality of detector modules, each sampling tube of the base is in fluid communication with a different air sampling path that progresses through a detector module of the plurality of detector modules, each detector module of the plurality of detector modules is connected via one or more inlet ports and one or more outlet ports thereon to corresponding inlet and outlet ports of the base, such that air to be tested is communicated from each sampling tube attached to the base to an air sampling path within the detector module to which it has a fluid connection and that each detector module is each independently releasably attached to the base, wherein the at least one pump draws the air from one of the plurality of sampling tubes into the air sampling path and into a particulate sensing chamber within the detector module.

9. The modular monitoring unit of claim 8, wherein at least one of the plurality of detector modules has a plurality of particulate sensing chambers therein and wherein each particulate sensing chamber is connected to one of the plurality of sampling tubes such that the air passes from the one of the plurality of sampling tubes into the particulate sensing chamber.

10. The modular monitoring unit of claim 9, wherein at least one of the plurality of detector modules is removable and replaceable by another detector module.

11. The modular monitoring unit of claim 8, wherein the modular monitoring unit also includes at least one of: a cable management module, a communication module, an air quality module, and a gas sensing module.

12. The modular monitoring unit of claim 8, wherein the at least one pump is provided in a pump module and wherein the pump module is removable and replaceable by another pump module.

13. The modular monitoring unit of claim 8, wherein each detector module includes a flow sensing chamber.

14. The modular monitoring unit of claim 8, wherein each detector module includes a filter.

15. The modular monitoring unit of claim 8, wherein each detector module is connected to a filtering cap.

16. The modular monitoring unit of claim 15, wherein the filtering cap is removable and replaceable with another filtering cap.

17. A modular monitoring system, comprising:
- a rack for mounting a number of modular monitoring units to a wall;
- a first modular monitoring unit mounted to the rack, including;
  - a base having a plurality of sampling tubes mounted thereon;
  - at least one pump; and
  - at least one detector module that is releasably attached to the base, wherein the at least one pump draws air from one of the plurality of sampling tubes into a particulate sensing chamber within a detector module of the at least one detector module; and
- a second modular monitoring unit mounted to the rack, including;
  - a different base having a plurality of different sampling tubes mounted thereon;
  - at least one different pump; and
  - at least one different detector module that is releasably attached to the different base, wherein the at least one different pump draws the air from one of the plurality of different sampling tubes into a different particulate sensing chamber within the at least one different detector module.

18. The modular monitoring system of claim 17, wherein the base and the different base each have an aperture formed therein for placement of a common conduit for positioning of at least one of a power cord and a communication cable.

19. The modular monitoring system of claim 17, wherein the base has a mounting plate and wherein the mounting plate is sized such that at least one different sampling tube of the plurality of different sampling tubes passes between a front surface of the mounting plate and a back surface of the base.

20. The modular monitoring system of claim 17, wherein the first modular monitoring unit has a pump module with the at least one pump therein.

* * * * *